United States Patent [19]

Salmasi et al.

[11] Patent Number: 5,679,887
[45] Date of Patent: Oct. 21, 1997

[54] METHOD OF ESTIMATING MECHANICAL HARDNESS OF STEEL FROM ITS MAGNETIC PROPERTIES

[75] Inventors: Zareh S. Salmasi, Cardiff; Hugh J. Stanbury, Ponthir Newport; Turgut Meydan, Cardiff; Anthony J. Moses, Dinas Powys; James H. R. Page, Machen; Philip Beckley, Betiws Newport, all of Great Britain

[73] Assignees: ORB Electrical Steels Limited; University College Cardiff Consultants Limited, both of Great Britain

[21] Appl. No.: 619,525

[22] PCT Filed: Oct. 24, 1994

[86] PCT No.: PCT/GB94/02337

§ 371 Date: Jun. 19, 1996

§ 102(e) Date: Jun. 19, 1996

[87] PCT Pub. No.: WO95/12821

PCT Pub. Date: May 11, 1995

[30] Foreign Application Priority Data

Oct. 30, 1993 [GB] United Kingdom ............. 9322431

[51] Int. Cl.$^6$ ............. G01R 33/12; B23Q 17/20; G01N 3/00
[52] U.S. Cl. ............. 73/78; 324/228
[58] Field of Search ............. 73/78, 83; 324/219, 324/220, 226, 228

[56] References Cited

U.S. PATENT DOCUMENTS

| | | | |
|---|---|---|---|
| 3,586,963 | 6/1971 | Arrott et al. | 324/34 |
| 4,710,712 | 12/1987 | Bradfield et al. | 324/227 |
| 5,109,195 | 4/1992 | Allison et al. | 324/235 |
| 5,121,058 | 6/1992 | Allison et al. | 324/226 |
| 5,134,368 | 7/1992 | Otaka et al. | 324/226 |

FOREIGN PATENT DOCUMENTS 2 031 155  4/1980  United Kingdom.

OTHER PUBLICATIONS

IEEE Transducer Conference, Washington, D.C., USA, 10–11 Feb. 1969, vol. ieci–16, ISSN 0018–9421, IEEE Transactions On Industrial Electronics and Control Instrumentation, Jul. 1969, USA, Gibson C. A. et al., "A Magnetic Means of Monitoring Hardness Due to Heat Treatment in Steel Production".

*Primary Examiner*—Elizabeth L. Dougherty
*Assistant Examiner*—Max H. Noori
*Attorney, Agent, or Firm*—Bacon & Thomas

[57] ABSTRACT

A method of estimating mechanical hardness of a steel by the measurement of a plurality of magnetic parameters of the steel, comprises the steps of estimating for each parameter one or more probable hardness ranges by reference to a stored set of hardness ranges and associated parameters and combining these estimates to provide an estimate of the hardness range. Preferably three parameters are measured and these may be coercivity, power loss and permeability. These parameters may be measured simultaneously.

7 Claims, 6 Drawing Sheets

METHOD OF ESTIMATING MECHANICAL HARDNESS OF STEEL FROM ITS MAGNETIC PROPERTIES

BACKGROUND OF THE INVENTION

1. Field of the Invention

This invention relates to testing of hardness steels. In particular, the invention relates to a method of estimating mechanical hardness of a steel from its magnetic properties.

2. Description of the Related Art

In the production of steel, and especially low-carbon non-oriented electrical steels, the hardness of the steel is one parameter which is frequently tested. In the continuous decarburisation annealing of electrical steels, hardness is sometimes used as a parameter to determine the correct working of a continuous processing line, but up till now it has only been measurable accurately by off-line mechanical means. This has meant that the line is often stopped and destructive testing of a sample undertaken.

It is known that the mechanical hardness of steels, particularly magnetically soft electrical steels but including hard steels, is related to the magnetic properties of the steel but in a way that is difficult to use for mechanical hardness determination.

SUMMARY OF THE INVENTION

It is an object of the present invention to provide a method of estimating mechanical hardness of steel from its magnetic properties.

According to the present invention in one aspect there is provided a method of estimating mechanical hardness of a steel, the method comprising the steps of determining a plurality of magnetic parameters of the steel, estimating for each such measured parameter one or more probable hardness ranges by reference to a stored set of hardness ranges and associated parameters and combining these estimates to provide an estimate of mechanical hardness of the steel.

Preferably three parameters are measured and these may be coercivity, power loss and permeability. The parameters may be measured simultaneously. For a magnetically soft steel, the steel may be enwrapped by a pair of coils the first carrying an alternating electrical current to apply to the steel an alternating magnetic field and the other measuring the magnetic flux density thereby induced, said measurements being used to determine the measured parameters.

In another aspect, the invention provides a method of estimating mechanical hardness of a steel, the method comprising the steps of measuring the mechanical hardness and magnetic parameters of a multiplicity of steel samples of like chemistry and storing these measured values in a data bank in a plurality of quantised groupings of hardness against each measured magnetic property, measuring a plurality of magnetic parameters of the steel whose hardness is to be estimated, comparing each such measured parameter with the quantised groupings of stored value of that parameter in the data bank to determined in which quantised grouping the parameter falls, comparing the determined quantised grouping for each measured parameter, and estimating thereon the mechanical hardness of the steel.

The invention will now be described by way of example and with reference to the accompanying drawings,

DESCRIPTION OF THE FIGURES OF DRAWINGS

DETAILED DESCRIPTION OF THE PREFERRED EMBODIMENT

Figure 1:
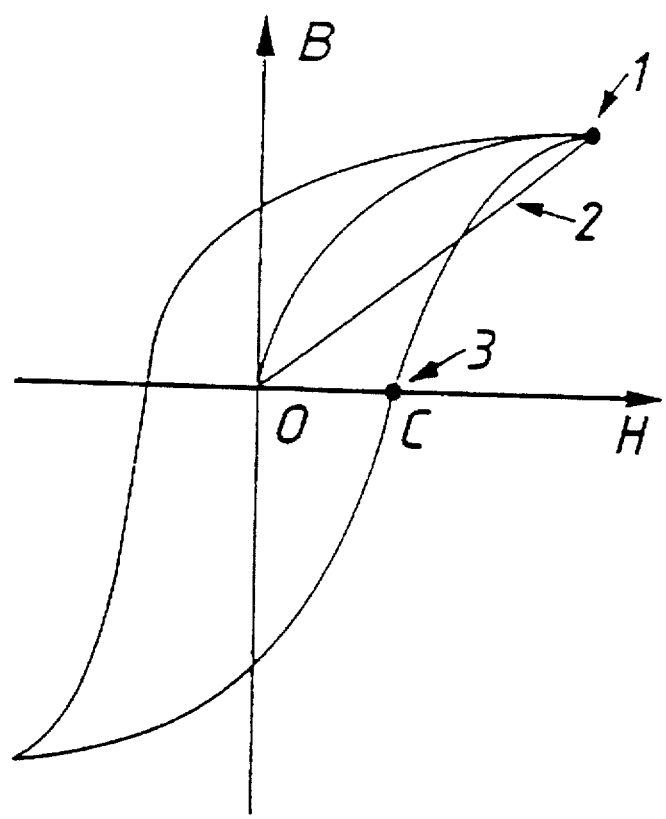
FIG. 1 is a typical hysteresis loop for a magnetic steel.

As has been explained, the magnetic parameters of steels show a correspondence to the mechanical hardness of the steel. Three parameters that have been shown to have a relationship with mechanical hardness are coercivity, power loss, and permeability. These standard parameters are illustrated in FIG. 1 which is a typical hysteresis loop showing the relationship of magnetic field strength H against magnetic flux density B for a typical material. It should be noted that, on the scales normally used, the H axis has been exaggerated in scale for clarity in respect of a typical magnetically soft electrical steel. The three parameters measured are firstly coercive field strength C, which is the magnetic field for zero magnetic flux density and is shown by point 3 in FIG. 1; secondly, relative permeability which has the symbol µr and is the gradient of line 2; and thirdly, power loss W, which is conventionally measured as the specific total loss in W/kg, and is the power absorbed by the material because the induction and field do not follow each other exactly, and is measured at a particular magnetic flux density for the present purposes.

Figure 2:
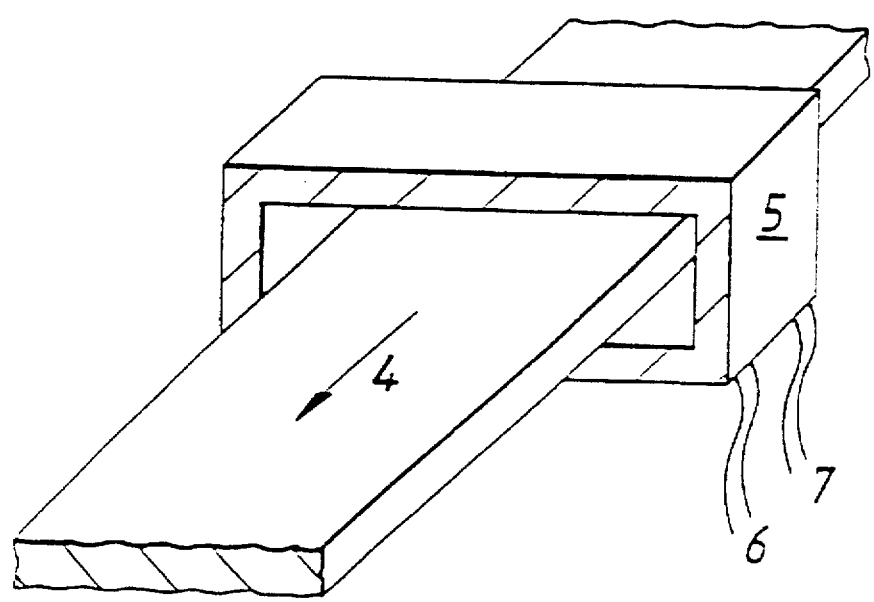
FIG. 2 is a schematic diagram of an arrangement of continuous tester for on-line magnetic measurements.

In operation the method has been applied to the estimation of the mechanical hardness of a continuously processed strip of electrical steel. This strip is shown diagrammatically in FIG. 2 moving along a processing line in the direction of the arrow 4. A coil carrier 5 enwraps the moving steel and is provided with two coils having input leads 6 and 7. Coil 6 carries a 50 Hz electrical current and generates a magnetic field designed to produce a peak magnetic flux density of 1.5 Tesla in the strip. Coil 7 is arranged in a conventional manner to measure the magnetic flux density produced by the field in the strip. Standard processing techniques are employed, preferably simultaneously, to extract from the input and output signals, measurements of the specific total loss W, relative permeability µr, and coercive field strength C.

Figure 3:
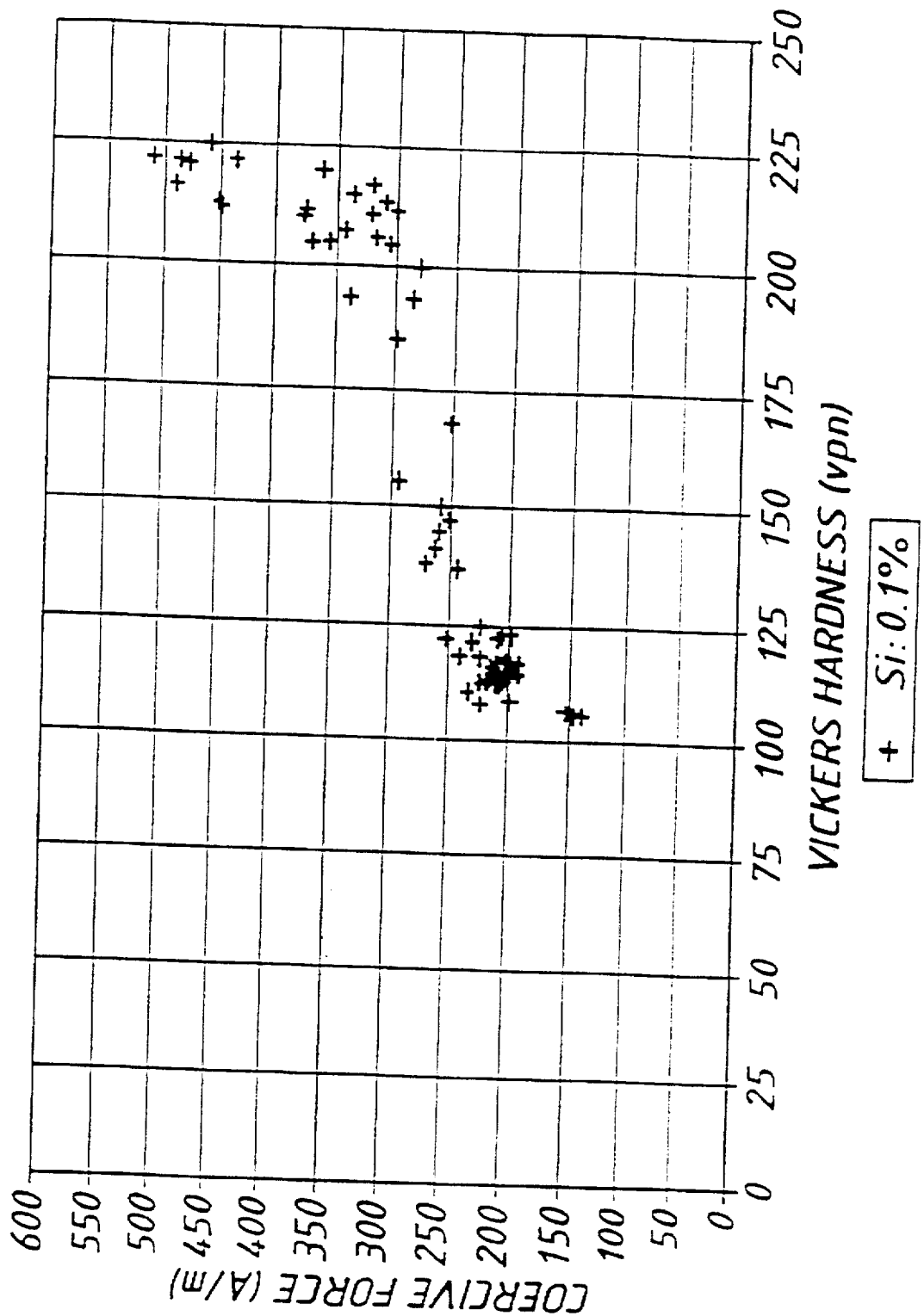
FIGS. 3, 4 and 5 show respectively the coercive field strength, specific total power loss and relative permeability against Vickers hardness for a silicon steel.
Figure 4:
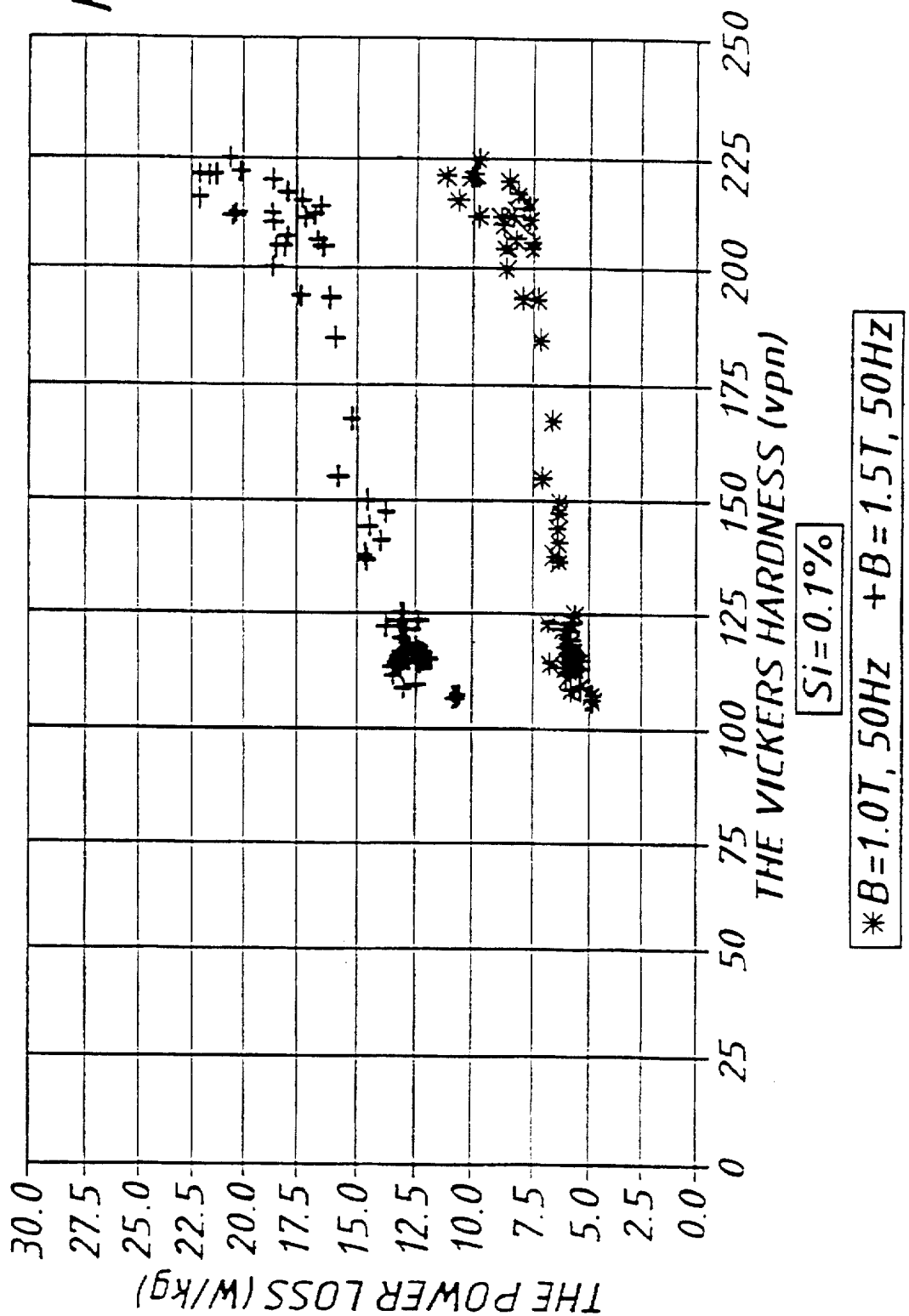
Figure 5:
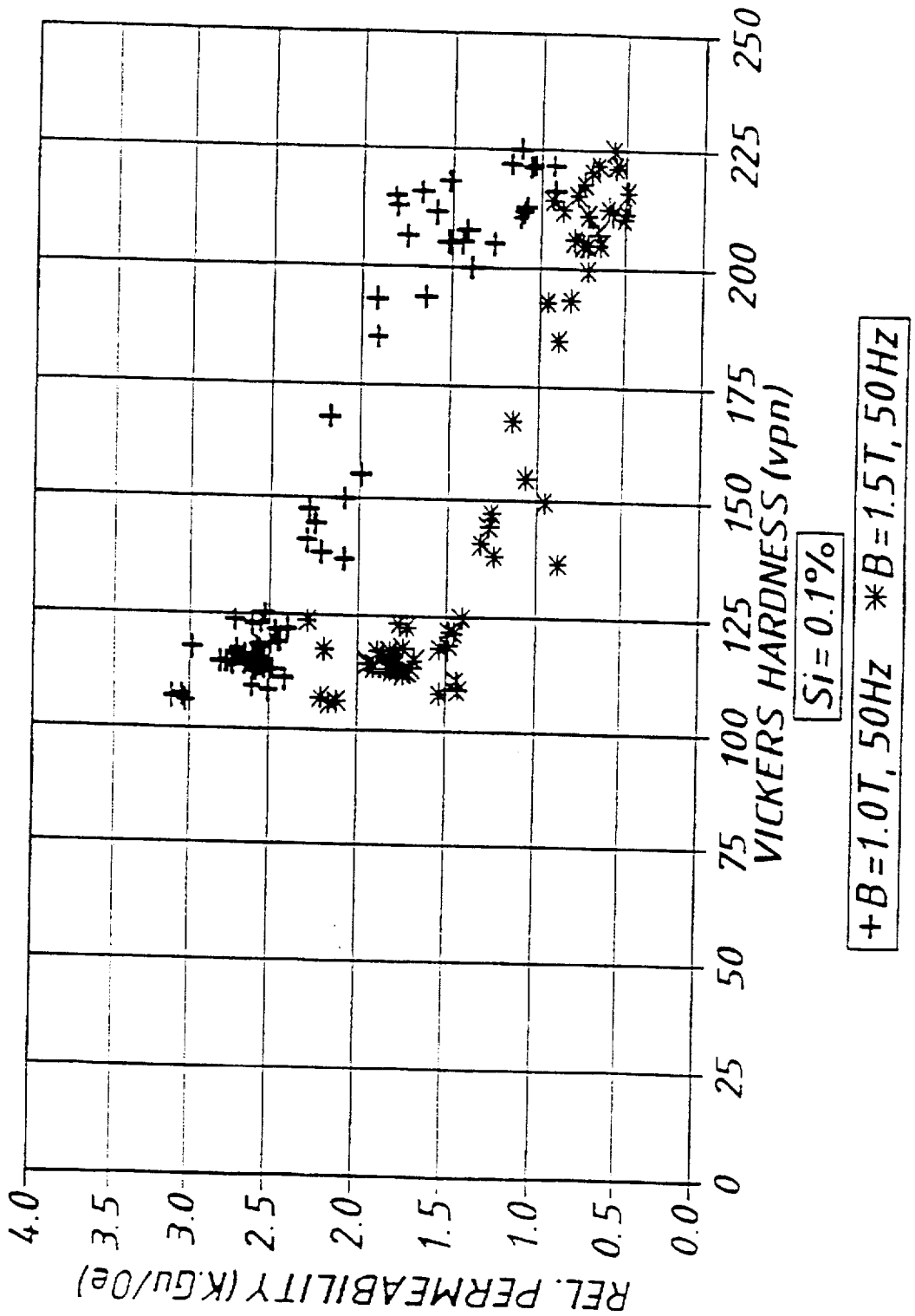

Such measurements are, of course, not new, but the difficulty of processing the results to predict mechanical hardness can be seen by turning to FIGS. 3, 4 and 5, which show for a typical low silicon electrical (magnetically soft) steel respectively coercive field strength C, power loss W and relative permeability µr.

These are plotted against Vickers hardness expressed as Vickers Pyramidal Number referred to as VPN and measured by offline mechanical testing. The silicon content of the steel in question is 0.1% and the peak magnetic flux density applied is 1.5 and 1.0 Tesla at 50 HZ as shown on the Figures. It can be seen that the results in general show that the parameters in each case move with the same general trend as changes in hardness but in a manner not capable of easy analytical solution. Indeed, statistical techniques using correlation have been tried and found to give highly unsatisfactory results for prediction purposes. The method of the present invention adopted to process the results is therefore important. The method starts with the creation of a databank. This is done by measuring the hardness of a large number of different samples and also their magnetic parameters. An individual databank for each chemistry of steel is produced. In this example, the silicon content of the steel is the parameter of steel chemistry that has been used, and therefore in analysing the results from magnetic testing the stored data corresponding to the silicon content nearest to that of the steel being measured are used.

The databank is arranged according to the method shown in Table 1. It should be noted that Table 1 shows the arrangement for the specific total power loss W; however, the tables for the selected other two parameters (coercive field strength and relative permeability) are exactly parallel and are not repeated.

A separate Table is constructed for each silicon content.

The steel samples were categorised by their mechanical hardnesses. Each sample measured was placed within a quantised grouping of Vickers hardness units (VPN), this being set by the expected resolution of the method. The power losses for the samples falling within each quantised grouping were then averaged to calculate the mean specific total loss and also the maximum and minimum of the range. The variance $\sigma$ for the samples falling within the quantised grouping was calculated together with the tolerance, this being the deviation from the mean within which 90% of the samples fall. These 90% assigned confidence levels are an estimate and have been found to be satisfactory for this particular application.

Each quantised grouping is identified by an alpha notation from A to AF, there being 32 quantised groupings in the databank used in this example. In operation the three parameters of specific total loss W, coercive field strength C and relative permeability are measured. Each measurement is then compared with the appropriate table of quantised groupings. Each measurement will fall within one or more of the ranges of specific total loss (or other parameter) within the tolerance levels previously set. Each range within which the measurement falls is stored, and that quantised grouping selected. Turning to Table 2, this process is diagrammatically represented. In this Table for one measurement the specific total loss W may fall within the ranges of the hardness quantised groupings P, R and S, while the relative permeability falls within the tolerance ranges for quantised groupings O, Q and R and that for the coercive field strength falls within the ranges for quantised groupings P, Q and R. It will be noted particularly that each measurement may fall within the range for two or more quantised groupings and indeed, because of the scatter of the initial data from which the database was created the groupings into which it falls may not be contiguous. The process then selects the quantised hardness grouping selected by most parameters (in the case of Table 2 grouping R) and uses this as the estimate of the mechanical hardness of the sample measured.

A refinement is that the standard deviation for each possible quantised grouping is measured and that having the smallest size is selected if there is an equality of votes. This enables a very broad range for a particular quantised grouping to be eliminated as a choice in favour of a more limited alternative.

The variants and tolerance are extracted and combined to provide an estimate of the Vickers hardness (VPN) and its limits.

Figure 6:
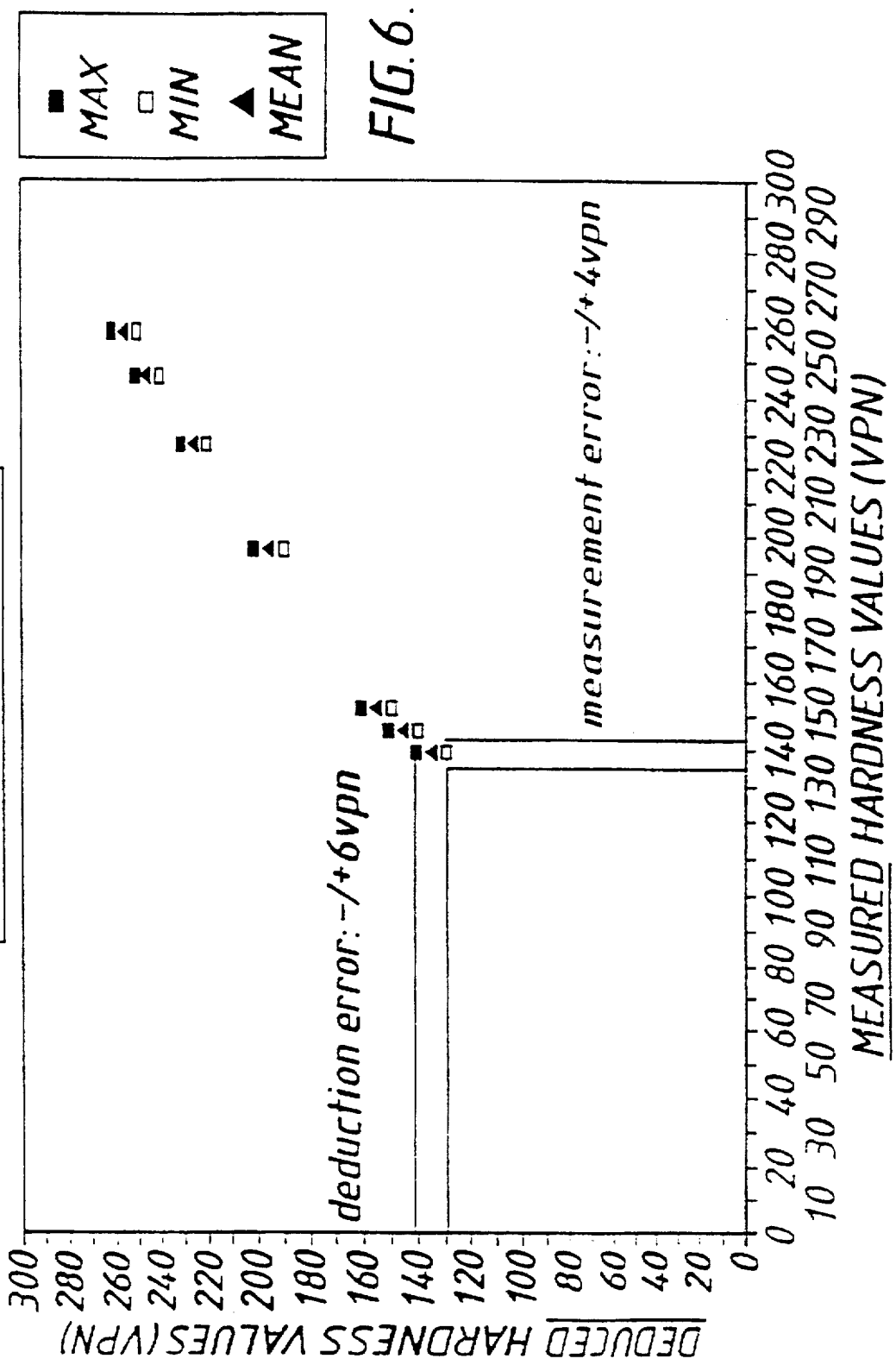
FIGS. 6 and 7 show the results of approximated hardnesses for two steels.
Figure 7:
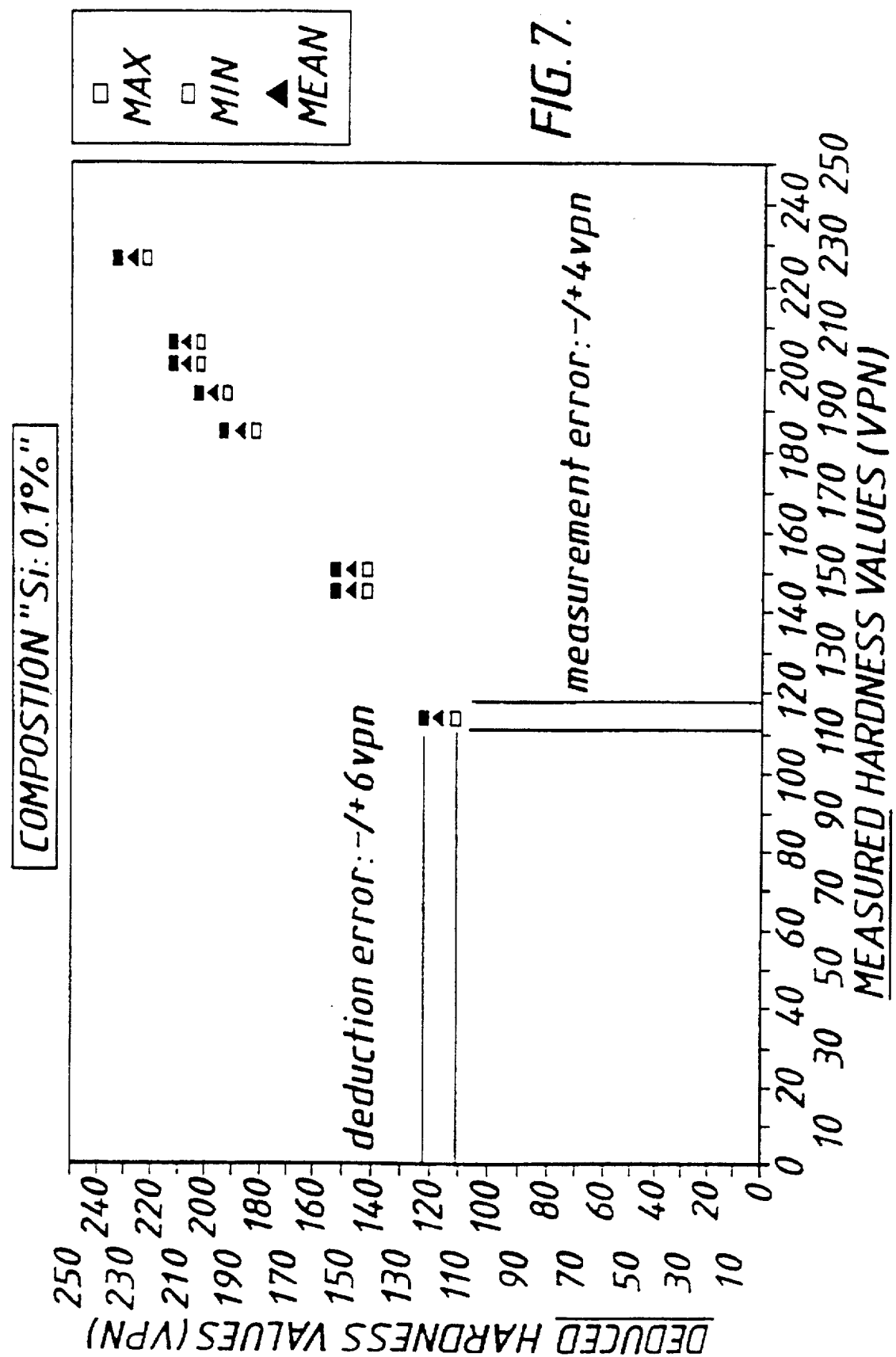

As an example of the use of this system of analysis the results for 0.1 and 1.3% silicon steels are shown respectively in FIGS. 6 and 7. The measured hardness is shown on the ordinate and the approximated ranges from magnetic measurements on the abscissa. The predicted ranges are shown and it will be seen that the measured hardness in all cases falls within the predicted range.

This method has been described with particular reference to the continuous processing of a magnetically soft electrical steel. This is not the only type of steel or other electrical material for which it can be employed.

Thus, the invention has application to hardness testing of relatively hard steels. For such testing, a steel strip may be passed over a three-head assembly, the first head being arranged to demagnetise the steel, the second to apply a magnetic pattern at a known induction and the third head to read the pattern remaining in the steel. Thus, the same three parameters referred to above—namely coercivity, power loss and permeability—can be determined.

Obviously the importance of each parameter in analysing the mechanical hardness of the steel varies with type of steel, but the method enables the parameters to be combined to produce an estimate over a wide range of materials. Obviously, databanks can be set up corresponding to different steel chemistries where it is known that these different steel chemistries produce significantly different results.

In operation, when used to monitor the performance of the annealing process in a continuous electrical steel production line, for example, the measured hardness ranges will be approximately the same, and therefore the data that is needed in the databanks is that corresponding to the expected hardness. A deviation, rather than an exact result, is what is generally required to be known.

It is possible that the results produced by the three magnetic parameter measurements will be widely dissimilar. This is suggestive of recrystallisation of the steel. What is happening is that the steel is beginning to lose its homogeneity and therefore the results of the measurement become widely disparate. Although no estimate of the mechanical hardness can be given, it is an indication of non-standard annealing process.

It will be appreciated that the foregoing is merely exemplary of methods of and apparatus for hardness testing in accordance with the invention and that modifications can readily be made without departing from the true scope of the invention.

TABLE 1

| Quantised grouping | Hardness | | Specific Power Loss | | Variance/Tolerance | |
|---|---|---|---|---|---|---|
| | Mean | Range | Mean | Range | | |
| A | $V_A$ | $V_1-V_2$ | $W_A$ | $W_1-W_2$ | $\sigma(W)_A$ | $t(W)_A$ |
| B | $V_B$ | $V_2-V_3$ | $W_B$ | $W_1-W_3$ | $\sigma(W)_B$ | $t(W)_B$ |
| C | $V_C$ | $V_3-V_4$ | $W_C$ | $W_3-W_4$ | $\sigma(W)_C$ | $t(W)_C$ |
| C | $V_C$ | $V_3-V_4$ | $W_C$ | $W_3-W_4$ | $\sigma(W)_C$ | $t(W)_C$ |
| C | $V_C$ | $V_3-V_4$ | $W_C$ | $W_3-W_4$ | $\sigma(W)_C$ | $t(W)_C$ |
| Q | $V_Q$ | $V_{17}-V_{18}$ | $W_Q$ | $W_{17}-W_{18}$ | $\sigma(W)_Q$ | $t(W)_Q$ |
| Q | $V_Q$ | $V_{17}-V_{18}$ | $W_Q$ | $W_{17}-W_{18}$ | $\sigma(W)_Q$ | $t(W)_Q$ |
| Q | $V_Q$ | $V_{17}-V_{18}$ | $W_Q$ | $W_{17}-W_{18}$ | $\sigma(W)_Q$ | $t(W)_Q$ |
| Q | $V_Q$ | $V_{17}-V_{18}$ | $W_Q$ | $W_{17}-W_{18}$ | $\sigma(W)_Q$ | $t(W)_Q$ |
| Z | $V_Z$ | $V_{26}-V_{27}$ | $W_Z$ | $W_{26}-W_{27}$ | $\sigma(W)_Z$ | $t(W)_Z$ |
| AA | $V_{AA}$ | $V_{27}-V_{28}$ | $W_{AA}$ | $W_{27}-W_{28}$ | $\sigma(W)_Z$ | $t(W)_Z$ |
| AB | $V_{AB}$ | $V_{28}-V_{29}$ | $W_{AA}$ | $W_{28}-W_{29}$ | $\sigma(W)_Z$ | $t(W)_Z$ |
| AB | $V_{AB}$ | $V_{28}-V_{29}$ | $W_{AB}$ | $W_{28}-W_{29}$ | $\sigma(W)_Z$ | $t(W)_Z$ |
| AF | $V_{AF}$ | $V_{32}-V_{33}$ | $W_{AF}$ | $W_{32}-W_{33}$ | $\sigma(W)_{AF}$ | $t(W)_{AF}$ |

TABLE 2

| Hardness Range | M | N | O | P | Q | R | S | T | U | V ... |
|---|---|---|---|---|---|---|---|---|---|---|
| Parameter | | | | | | | | | | |
| Specific total W Loss | | | | P | | R | S | | | |
| Relative | | | O | | Q | R | | | | |

TABLE 2-continued

| Hardness Range | M | N | O | P | Q | R | S | T | U | V... |
|---|---|---|---|---|---|---|---|---|---|---|
| Permeability μr | | | | | | | | | | |
| Coercive C Field Strength Selected Range Votes... | | | | P | Q | R | | | | |

We claim:

1. A method of estimating mechanical hardness of a steel the method comprising the steps of determining a plurality of magnetic parameters of the steel, estimating for each such measured parameter one or more probable hardness ranges by reference to a stored set of hardness ranges and associated parameters and combining these estimates to provide an estimate of the mechanical hardness of the steel.

2. A method as claimed in claim 1 wherein the determined parameters are coercivity, power loss and permeability.

3. A method as claimed in claim 1 wherein the parameters are measured simultaneously.

4. A method as claimed in claim 1 wherein the steel is enwrapped by a pair of coils the first carrying an alternating electrical current to apply to the steel an alternating magnetic field and the second measuring the magnetic flux density thereby induced.

5. A method of estimating mechanical hardness of a steel, the method comprising the steps of measuring the mechanical hardness and magnetic parameters of a multiplicity of steel samples of like chemistry and storing these measured values in a data bank in a plurality of quantised groupings of hardness against each measured magnetic property, measuring a plurality of magnetic parameters of the steel whose hardness is to be estimated, comparing each such measured parameter with the quantised groupings of stored value of that parameter in the data bank to determined in which quantised grouping the parameter falls, comparing the determined quantised grouping for each measured parameter, and estimating thereon the mechanical hardness of the steel.

6. A method as claimed in claim 5 wherein the measured magnetic parameters of the steel include coercivity, power loss and permeability.

7. A method as claimed in claim 6 wherein the measured magnetic parameters and measured simultaneously.

* * * * *